United States Patent [19]

Krause

[11] 4,292,962

[45] Oct. 6, 1981

[54] APPARATUS FOR POSTURAL TREATMENT OF HUMANS

[76] Inventor: Nicolaas J. P. R. Krause, 35 Machine St., Elsburg, Transvaal Province, South Africa

[21] Appl. No.: 31,518

[22] Filed: Apr. 19, 1979

[51] Int. Cl.³ .............. A61F 5/00

[52] U.S. Cl. .............. 128/68; 128/24 R; 272/49; 272/93

[58] Field of Search .............. 128/68, 69, 71, 72, 128/73, 74, 75, 84 R, 24 R; 272/55, 56, 49, 144, 145, 134, 93; 269/323, 324, 325, 326

[56] References Cited

U.S. PATENT DOCUMENTS

| | | | |
|---|---|---|---|
| 1,301,071 | 4/1919 | Marshall | 128/73 |
| 1,427,004 | 8/1922 | McManis | 128/73 |
| 2,110,069 | 3/1938 | McGaw | 128/74 |
| 2,228,793 | 1/1941 | Swofford | 128/72 |
| 2,475,289 | 7/1949 | MacGregor | 128/68 |
| 3,286,708 | 11/1966 | Gärtner | 128/24 R |
| 3,293,667 | 12/1966 | Ohrberg | 128/68 |
| 3,302,641 | 2/1967 | Berne et al. | 128/71 |
| 3,568,669 | 3/1971 | Stites | 128/71 |
| 3,722,507 | 3/1973 | Krause | 128/68 |
| 4,170,988 | 10/1979 | Krause | 128/68 |

FOREIGN PATENT DOCUMENTS

| | | | |
|---|---|---|---|
| 808146 | 7/1951 | Fed. Rep. of Germany | 128/71 |
| 2247285 | 3/1974 | Fed. Rep. of Germany | 128/74 |
| 766568 | 6/1934 | France | 269/325 |

*Primary Examiner*—Kyle L. Howell
*Assistant Examiner*—Arthur S. Rose

[57] ABSTRACT

An apparatus for effecting postural treatment of humans. The apparatus includes a pivoting platform structure pivotally mounted on a stand. The platform structure is such that a person can be supported in the region of his hip in a bent over, face down attitude and an adjusting mechanism is provided whereby the position of the platform relative to the pivotal axis may be varied. By such adjustment of the pivotal axis, the center of gravity of a person supported on the platform can be adjusted and in particular can be adjusted in such a way that a person, supported on the platform, can control pivoting of the platform by varying the position of his arms.

24 Claims, 6 Drawing Figures

APPARATUS FOR POSTURAL TREATMENT OF HUMANS

BACKGROUND OF THE INVENTION

This invention relates to postural treatment of humans. The invention relates in particular to an apparatus for effecting postural treatment of humans.

SUMMARY OF THE INVENTION

According to the invention there is provided an apparatus for effecting postural treatment of humans, the apparatus including a supporting structure; and a platform structure, that is pivotally mounted on the supporting structure to be pivotal about a horizontal pivotal axis, which has a platform on which a human may be supported in the region of his hip, in a bent over, face down attitude, and which has an adjusting mechanism whereby the position of the platform relative to the platform structure and thus the pivotal axis may be varied so that the position of the centre of gravity of the platform and a person supported thereon, relative to the pivotal axis, can be adjusted.

The adjusting mechanism may be such that the position of the platform relative to the pivotal axis can be varied so that the centre of gravity of the platform and a person supported thereon may be displaced from one side of the pivotal axis to the other by varying the position of a part of the person's body.

Conveniently, the centre of gravity may be displaced by the person varying the position of his arms.

Thus, the platform may be such that when a person is not supported thereon it tends to assume an initial position, hereinafter termed the 'upright' position. In this position the platform is disposed with a portion thereof, which is engaged in use by the hip and thighs of the person, in a substantially vertical position. The platform is then pivoted, in use, into a position—the 'inverted' position—in which the said hip and thigh engaging portion is substantially horizontally disposed. Accordingly, the platform may be such, and may be so pivotally mounted, that when it supports a person, the centre of gravity of the person and the platform in combination, is on the side of the pivotal axis on which the person's head is located when the person extends his arms beyond his head, and is on the other side when the person retracts his arms towards his knees.

The platform may be radially displaceable with respect to the pivotal axis.

Thus, the platform may be adjustable in two mutually orthogonal radial directions so that in use the centre of gravity of the person and the platform may be suitably located to be displaced from one side of the pivotal axis to the other when the person extends and retracts his arms.

The adjusting mechanism may be infinitely and continuously variable.

The platform may be of substantially angular form to fit into the angle defined at the hip of a human whose torso is bent relative to his thighs. The platform may in one form be of L-shape to thereby define two limbs, the angle included between the limbs of the platform being about 90 degrees.

A fulcrum may be provided on the supporting structure to pivotally support the platform structure. The platform structure may be mounted in trunnion fashion in or on the supporting structure. Conveniently, the position of the pivotal mounting of the platform structure on the supporting structure may be adjustable to permit humans of different lengths to be supported on the platform. This may be effected by providing a number of sets of apertures in the supporting structure in which two pins projecting from the platform structure may be engaged.

In order to prevent the platform structure from executing a dangerous manoeuvre such as overturning, a stop may be provided on the supporting structure against which the platform structure may abut. The position of the stop may be adjustable. The platform structure may have foot rests on which a person may position himself prior to leaning over onto the platform to cause the platform structure to pivot. The distance of the foot rests from the fulcrum may also be adjustable.

If desired, a bracket may be provided fast with and extending from the platform structure to grip the legs of a user in the vicinity of his calves to prevent the user from tipping over and falling off the platform. The position of this bracket may also be adjustable.

In a preferred form, the adjusting mechanism may be screw-threadedly adjustable. Thus, the platform structure may have a 'T'-bar the trunnion pins projecting from the arms of the 'T'. The foot rest may then be telescopically slidable in the leg of the 'T'. The platform may then be secured to a support member which is telescopically adjustable in an intermediary member which is pivotally attached to the bottom of the leg of the 'T'. The distance of the platform from the arm may then be varied by pivoting the auxiliary member away from the arm by means of a screwthreaded nut and bolt arrangement. The platform may further be displaced in a direction parallel to that of the leg of the 'T', by telescopically displacing it by means of a further screw-threaded nut and bolt arrangement.

A cushion may be provided on which the chest of a person using the apparatus is supported. This chest support cushion may also be adjustable.

Finally, the platform structure may be provided with a counterweight extending beyond the pivotal axis in a direction opposite to that of the foot rest.

The invention is now described by way of an example with reference to the accompanying drawings.

DESCRIPTION OF PREFERRED EMBODIMENTS

Figure 1:
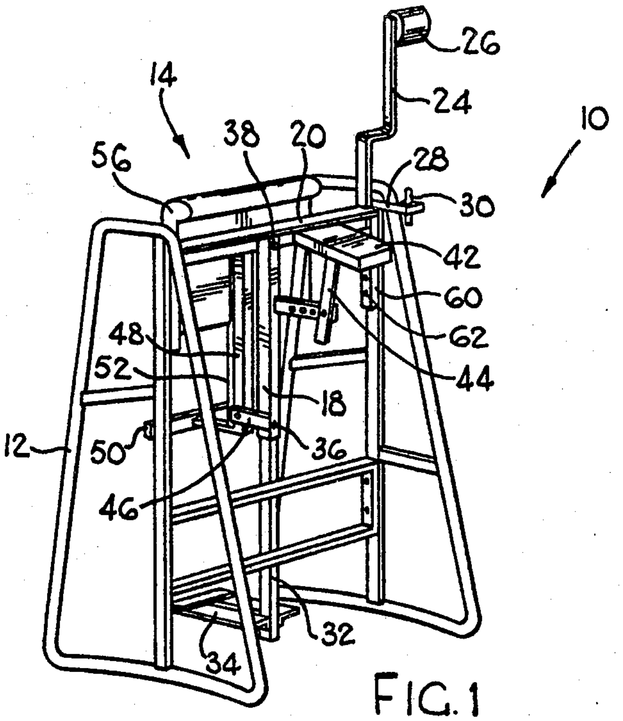
FIG. 1 shows a three dimensional view of an apparatus in accordance with the invention, from the rear, with the platform structure of the apparatus in the upright position.
Figure 2:
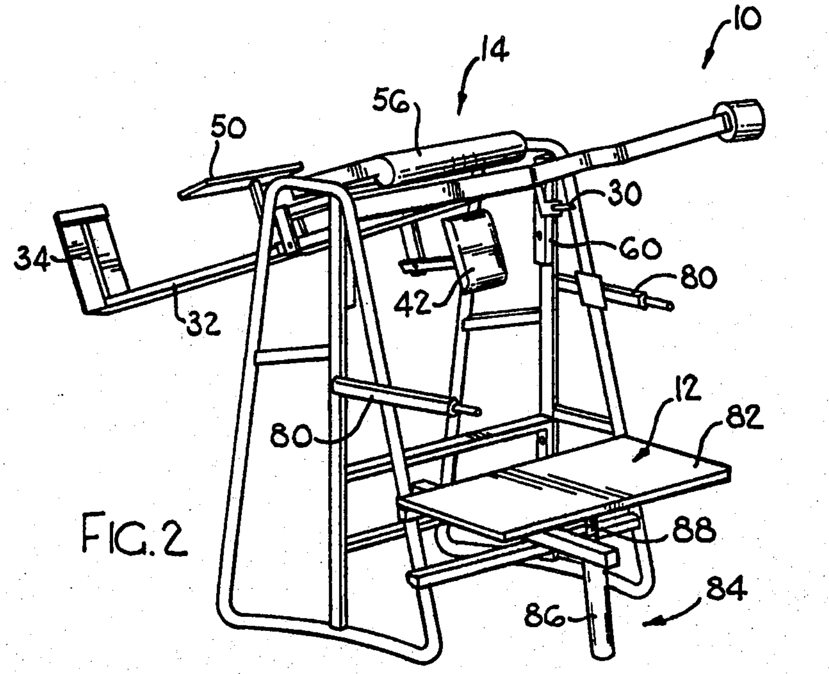
FIG. 2 shows a three dimensional view similar to that of FIG. 1 but with the platform structure in a pivoted, inverted position.
Figure 3:
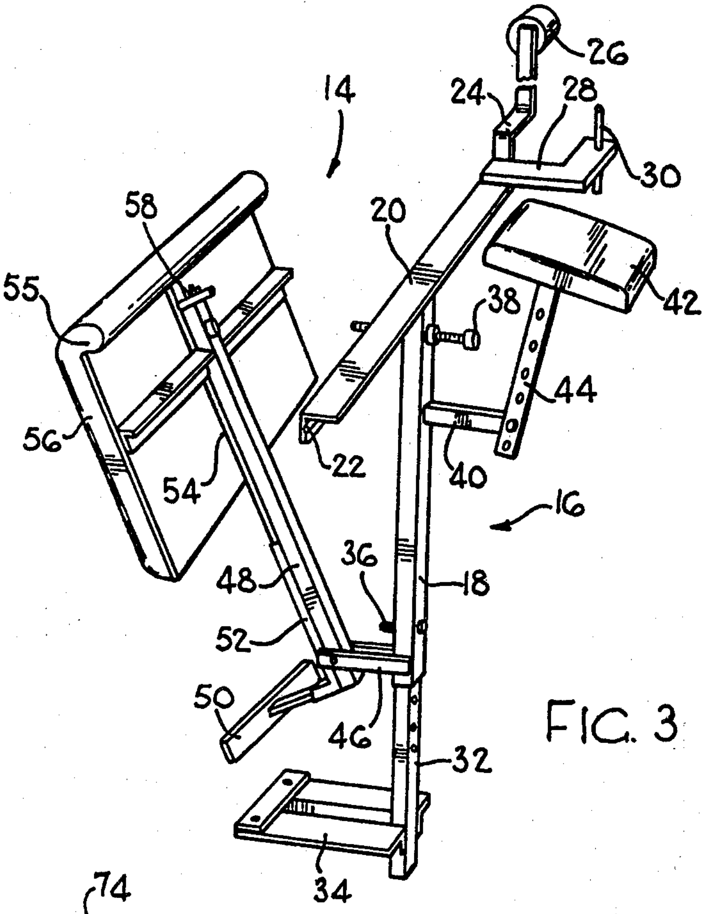
FIG. 3 shows a three dimensional view of the platform structure of the apparatus.

Referring to FIGS. 1 and 2, the apparatus is designated generally by reference numeral 10. The apparatus comprises a stand 12 and a pivoting platform structure 14, the platform structure 14 being shown in more detail in FIG. 3. Referring to FIG. 3, it can be seen that the platform structure 14 comprises a 'T'-bar 16 having an upright portion 18 and a cross member 20. At the ends of the cross member 20 are pins 22. Extending upwardly from one end of the cross member 20 is an arm 24 having at its end a countermass 26. A further member 28 is provided extending transversely from the cross member 20, which member 28 has at its free end a screw-threaded stud 30 which acts as a stop formation as will be explained hereinafter. The upright member 18 is hollow and slidably located therein is a length of tubing 32 which has at its free end two foot rests 34. The position of the tubing 32 in the upright member 18 may be fixed by means of a peg 36 which is received in a bore in the upright member 18. A number of bores are provided in the tubing 32 so that the distance of the foot rests 34 from the cross member 20 may be varied.

At the top end of the upright member 18 there is a transversely extending screw-threaded bore in which a screw-threaded bolt 38 is inserted. Extending transversely from the upright member 18, and secured thereto, is a bracket 40 to the free end of which is removably secured a chest support cushion 42. The chest support cushion 42 is secured to the bracket 40 by means of a rod 44 having a number of bores therein, the rod being variably secured to the bracket 40 by means of a nut and bolt arrangement. A further bracket 46 is secured to the bottom end of the upright member 18 extending transversely in an opposite direction to the bracket 40. Pivotally attached to the free end of this bracket 46 is an auxiliary support member 48. The support member 48 is secured at its bottom end to the bracket 46 by means of a nut and bolt. Extending away from the bracket 46 is a further 'T' member 50 the arms of which are padded and in use engage the calves of a person utilising the apparatus 10, to restrain the body of the person. The length of the leg of the 'T'-bar 50 may also be varied in a telescopically slidable manner. Secured to the bottom end of the support member 48 is a hollow member 52 in which is slidingly received a bar 54 to which is attached an L-shaped platform 56. The position of the bar 54 in the hollow member 52 may be varied by adjusting a screw-threaded nut and bolt arrangement 58 which is received in a bore in the upper end of the member 48 and on which a flange 55, fast with the bar 54, rests. It will thus be appreciated that the position of the platform 56 relative to the cross member 20 may be varied in two mutually orthogonal transverse directions by adjusting the bolt 38 and the nut and bolt 58.

Referring once more to FIGS. 1 and 2, the stand 12 has two spaced apart vertically disposed members 60 (only one of which is shown) having a number of apertures 62 in which the pins 22 of the platform structure 14 are received. These members 60 accordingly provide the fulcrum on which the platform structure 14 is pivotally mounted by means of the pins 22. It will thus be appreciated that the height of the cross member 20, and accordingly the pivotal axis of the platform structure 14, above the surface on which the stand 12 is supported may be varied. As can be seen in FIG. 2, the stud 30 engages one of the members 60 upon pivoting of the platform structure 14, to limit pivoting thereof.

Use of the apparatus 10 is now described with reference to FIGS. 4, 5 and 6.

Figure 4:
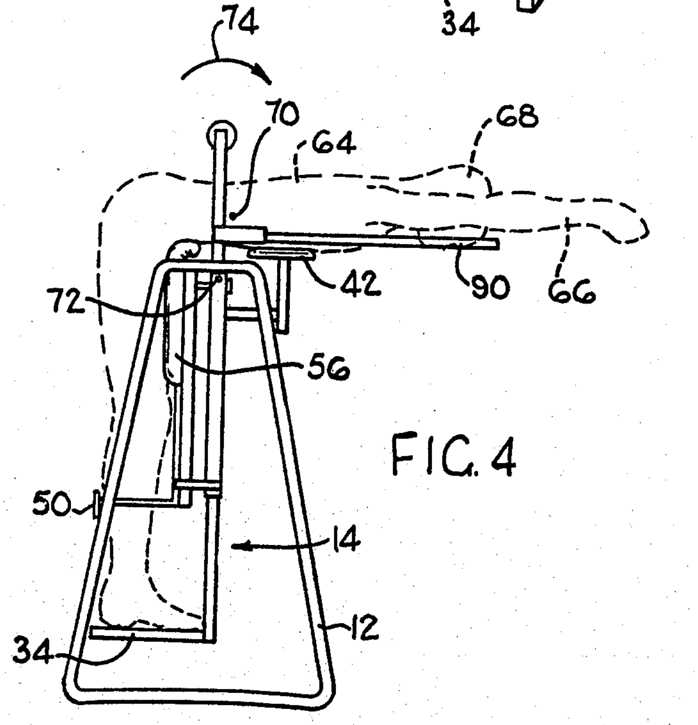
FIG. 4 shows diagrammatically a side view of the apparatus of FIG. 1 with the platform in an upright position immediately prior to being operated.

In FIG. 4 the platform 56 is shown in the upright position, with a person 64 standing on the foot rests 34 and being supported thereon and on the chest support cushion 42, in a bent over, face down manner. With the person's arms 66 extended beyond his head 68, the centre of gravity of the person 64 and the platform structure 14 is at 70, on the side of the pivotal axis 72 on which the person's head 68 is located-to the right of the pivotal axis 72 in FIG. 4. As the centre of gravity is above the pivotal axis 72, the platform structure 14 and the person 64 are in unstable equilibrium and the platform structure 14 pivots in the direction of arrow 74 until the stop 30 engages the member 60 to adopt the position shown in FIG. 5, with the person's torso substantially vertically disposed and with his legs substantially horizontally disposed.

Figure 6:
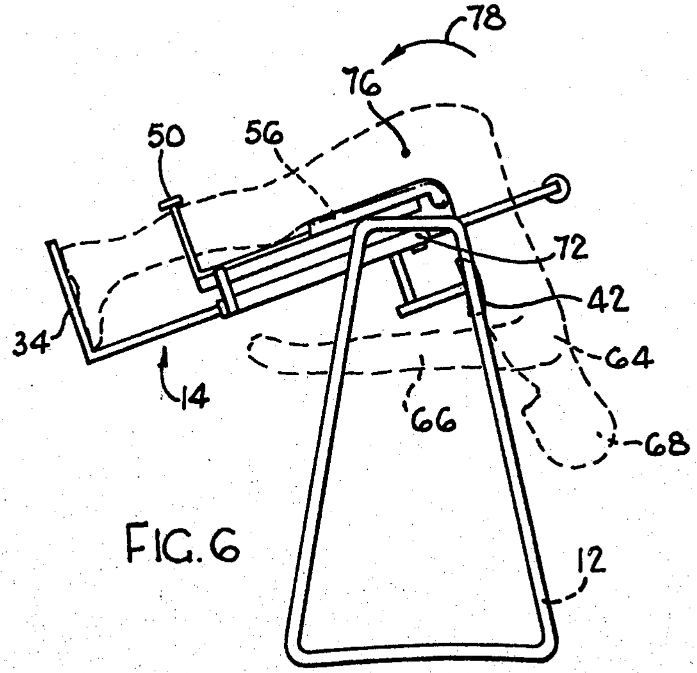
FIG. 6 shows the apparatus of FIG. 4 and the manner in which the platform is pivoted back to its upright position.

In order to pivot the platform structure back to the upright position the person retracts his arms towards his knees, as shown in FIG. 6. This causes the centre of gravity to be displaced to the other side of the pivotal axis 72, as shown at 76. The platform structure 14 thus pivots back, as shown by arrow 78 to the upright position.

It will further be appreciated that the position of the platform 56 is adjusted, by adjusting the bolt 38 and the nut and bolt 58, so that the centre of gravity is suitably located in accordance with the size and shape of the person using the apparatus. The foot rests 34, the 'T'-bar 50, the chest support cushion 42, and the height of support of the pins 22 are also suitably adjusted to cater for the particular person using the apparatus.

Further optional additions to the apparatus to ensure the comfort and safety of persons using the apparatus may include two arm supports 80 secured to each side of the stand 12 (only shown in FIG. 2). A person mounting the apparatus can use these supports for tilting himself slowly from an upright position into an inverted position. Furthermore a head support 82 may be provided (also only shown in FIG. 2). The head support 82 is secured to the stand 12 and includes a base 84, also secured to the stand 12 which base includes a base member 86 which stands on the ground and a screw-threaded member 88 which can screw into a bore in the base member 86. The member 88 provides a support beneath the head support 82 and provides adjustment of the head support 82 by being screwed into or from the base member 86.

In FIG. 4 there is shown an additional arm rest 90 secured to the platform structure 14. The rest 90 provides a support for a person to rest his arm on during use of the apparatus. A rest 90 as shown may be provided for one or both of the arms of a person using the apparatus.

Figure 5:
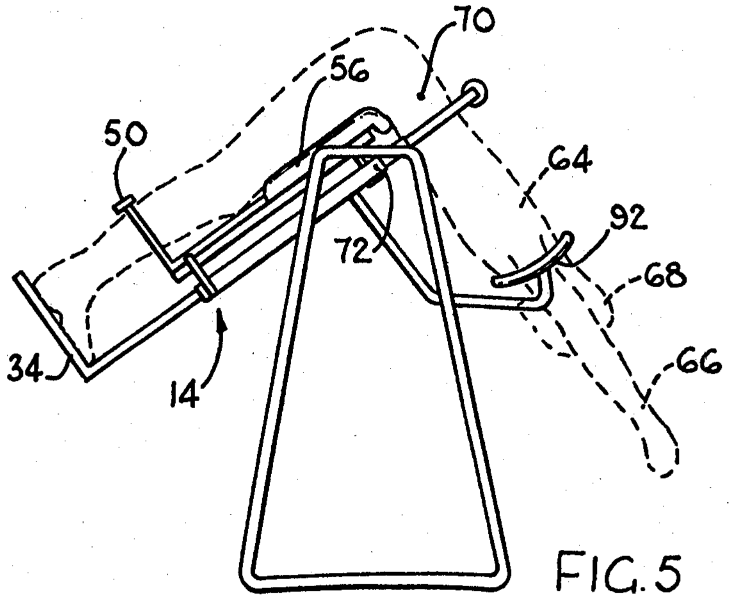
FIG. 5 shows the apparatus of FIG. 3 when operated.

FIG. 5 shows an alternative support for the chest cushion support 42 in the form of a shoulder support 92 in which a person can rest his shoulders when inverting himself on the apparatus.

I claim:

1. An apparatus for effecting postural treatment of humans, the apparatus including

- a supporting structure;
- a platform structure that is pivotally mounted on the supporting structure to be pivotal about a horizontal pivotal axis;

a platform adjustably secured on the platform structure, having a support surface on which a human may be supported in the region of his hip in a bent over, face down attitude;

a first adjusting mechanism for adjusting the position of the platform relative to the platform support structure in a first direction transverse to the pivotal axis of the platform support structure; and a second adjusting mechanism for adjusting the position of the platform relative to the platform support structure in a second direction transverse to the pivotal axis of the platform support structure and substantially orthogonal to the first direction, the position of the centre of gravity of the platform and a human supported thereon thus being adjustable relative to the pivotal axis of the platform support structure.

2. An apparatus as claimed in claim 1, in which the support surface of the platform faces away from the pivotal axis of the platform support structure so that the centre of gravity of the platform and a human supported thereon is located above the pivotal axis to thereby be adjustable to provide a condition of unstable equilibrium.

3. An apparatus as claimed in claim 2, in which the first and second adjusting mechanisms are such that the position of the platform relative to the platform support structure and thus the pivotal axis thereof can be varied so that the centre of gravity of the platform and a human supported thereon may be displaced from one side of the pivotal axis to the other by varying the position of a part of the human's body.

4. An apparatus as claimed in claim 3, in which the centre of gravity is displaceable by the human varying the position of his arms.

5. An apparatus as claimed in claim 1, in which the first and second adjusting mechanisms provide, within practical limits, infinite and continuous adjustability of the platform.

6. An apparatus as claimed in claim 5, in which the first and second adjusting mechanisms are screw-threadedly adjustable.

7. An apparatus as claimed in claim 6, in which the platform support structure has a "T"-bar with the arms of the "T"-bar extending parallel to and coinciding with the pivotal axis of the platform support structure and the leg of the "T"—bar extending perpendicular thereto, and in which the platform is secured to a support member which is telescopically adjustable in an intermediary member which intermediary member is pivotally attached to the leg of the "T"-bar near the free end thereof.

8. An apparatus as claimed in claim 7, in which the first adjusting mechanism includes a screw-threaded nut and bolt arrangement for pivotally adjusting the angular relationship between the leg of the "T"-bar and the intermediary member and thus the distance between the platform and the arms of the "T"-bar.

9. An apparatus as claimed in claim 7, in which the second adjusting mechanism includes a screw-threaded nut and bolt arrangement for telescopically displacing the platform relative to the intermediary member and thus substantially longitudinally with respect to the leg of the "T"-bar.

10. An apparatus as claimed in claim 1, in which the platform is of a substantially angular form to fit into the angle defined at the hip of a human whose torso is bent relative to his thighs.

11. An apparatus as claimed in claim 1, in which the platform support structure is pivotally mounted in trunnion fashion in or on the supporting structure.

12. An apparatus as claimed in claim 11, in which the pivotal mounting of the platform support structure on the supporting structure is adjustable to permit humans of different lengths to be supported on the platform.

13. An apparatus as claimed in claim 12, in which the supporting structure is provided with a number of sets of opposed apertures in which two pins projecting from the platform support structure may be engaged.

14. An apparatus as claimed in claim 1, which includes a countermass fast with the platform support structure to facilitate pivoting of the platform support structure with a human being supported on the platform.

15. An apparatus as claimed in claim 1, in which the platform support structure includes footrests on which a person may position himself prior to leaning over onto the platform to be supported thereon.

16. An apparatus as claimed in claim 15, in which the distance between the footrests and the pivotal mounting of the platform support structure to the supporting structure is adjustable.

17. An apparatus as claimed in claim 1, which includes a stop on the supporting structure against which the platform support structure may abut to prevent overturning thereof.

18. An apparatus as claimed in claim 17, in which the position of the stop is adjustable to vary the extent of turning of the platform support structure.

19. An apparatus as claimed in claim 1, which includes a bracket fast with and extending from the platform support structure, which bracket is positionable behind the legs of a human supported on the platform in the vicinity of his calves to thereby prevent him from tipping over and falling from the platform.

20. An apparatus as claimed in claim 1, which includes a chest support on which the chest of a human supported on the platform can be supported.

21. An apparatus as claimed in claim 20, in which the position of the chest support is adjustable.

22. An apparatus as claimed in claim 1, which includes a shoulder support on which the shoulders of a human supported on the platform can be supported.

23. An apparatus as claimed in claim 1, which includes a head support on which the head of a person supported on the platform can be supported.

24. An apparatus as claimed in claim 23, in which the position of the head support is adjustable.

* * * * *